United States Patent [19]

Schweikert et al.

[11] Patent Number: 4,598,072
[45] Date of Patent: Jul. 1, 1986

[54] COMBINATIONS OF AN AROMATASE-INHIBITOR AND AN ANTIANDROGEN FOR PROPHYLAXIS AND/OR TREATMENT OF BENIGN PROSTATIC HYPERPLASIA

[75] Inventors: Hans-Udo Schweikert, Bonn-Roettgen; Ulf Tunn; Theodor Senge, both of Castrup-Rauxel; Friedmund Nümann, Berlin, all of Fed. Rep. of Germany

[73] Assignee: Schering Aktiengesellschaft, Berlin and Bergkamen, Fed. Rep. of Germany

[21] Appl. No.: 448,673

[22] Filed: Dec. 10, 1982

Related U.S. Application Data

[63] Continuation-in-part of Ser. No. 307,332, Sep. 30, 1981, abandoned, and a continuation-in-part of Ser. No. 307,331, Sep. 30, 1981, abandoned.

[30] Foreign Application Priority Data

May 10, 1982 [GB] United Kingdom ............... 8213407

[51] Int. Cl.$^4$ ..................... A01N 45/00; A61K 31/56
[52] U.S. Cl. ..................................... 514/170; 514/171
[58] Field of Search ................. 424/240; 514/170, 171

[56] References Cited

U.S. PATENT DOCUMENTS

| | | | |
|---|---|---|---|
| 3,423,507 | 1/1969 | Neri ...................................... | 424/243 |
| 4,055,641 | 10/1977 | Benson et al. ....................... | 424/243 |
| 4,235,893 | 11/1980 | Brodie et al. ...................... | 260/397.4 |
| 4,310,523 | 1/1982 | Jovanovics et al. .............. | 260/397.4 |

FOREIGN PATENT DOCUMENTS 0100566  6/1983  European Pat. Off. ......... 260/397.4

OTHER PUBLICATIONS

Schwarzel et al., "Endocrinology" (1973) vol. 92, No. 3, pp. 866-880.
Chemical Abstracts, vol. 92 (1980) Par. 203,580m—by Newmann et al.
Physicians Desk Reference, 27th Ed. (1973), p. 1412.
Akhtar, Muhammed et al., J.C.S. Chem. Comm., 1981, pp. 129-130.
Robert W. Brueggemeier et al., Journal of Medicinal Chemistry, 1978, vol. 21, No. 10, pp. 1007-1011.
Schweikert, Horm. Metab. Res. 11, 635-640 (1979).
Schweikert et al., Excerpta Medica, Ed: Schroeder et al., pp. 126-133 (1980).
Schweikert, Excerpta Medica, Ed: Hamerstein et al. (1979), Amsterdam, Oxford, Princeton.
Weinstein et al., J. Clin. Invest. 53, 1-6 (1974).
McDonald et al., J. Clin. Endocrinol. Metabl. 27, 1103-1111 (1967).
Vigersky et al., J. Clin. Endocrin. and Metabl. 52, pp. 897-902 (1981).
Barone et al., J. Clin. Endocrin. and Metab. 49, 672-676 (1979).
Marynick et al., J. Clin. Endocrin and Metab. 49, 396-398 (1979).
Siiteri et al., J. Ster. Biochem. 6, 317-332 (1975).
Korenman (Geller/Albert) Endocrine Aspects of Aging, Elsevier Science Publishing Co., Inc. (1982) pp. 137-139.
Schwarzel et al., Endocrinology 92, p. 866 (1973).
Funk et al., Acta Endocrinologica 1982, 100:462-472.
Grayhack (Franks, Brendler) National Institute of Health, Feb. 20-21, 1975 DHEW Publication No. 76-1113, pp. 63-71, 85, 101-103.
Hinman, Jr. (Tannenbaum, DeKlerk) Springer-Verlag, New York, pp. 64-67, 69, 71-72; 262-268.

Primary Examiner—Elbert L. Roberts
Attorney, Agent, or Firm—Millen & White

[57] ABSTRACT

A combination of an aromatase-inhibitor and an antiandrogen in a weight ratio of aromatase-inhibitor to antiandrogen of 20:1 to 1:1 is useful in a method of prophylaxis and/or of treatment by therapy of prostatic hyperplasia. The aromatase-inhibitor is, for example, testolactone and the antiandrogen is, for example, cyproterone acetate.

47 Claims, No Drawings

COMBINATIONS OF AN AROMATASE-INHIBITOR AND AN ANTIANDROGEN FOR PROPHYLAXIS AND/OR TREATMENT OF BENIGN PROSTATIC HYPERPLASIA

CROSS-REFERENCE TO RELATED APPLICATION

This application is a continuation-in-part of U.S. application Ser. No. 307,332 of Sept. 30, 1981 and of U.S. application Ser. No. 307,331, of Sept. 30, 1981, both now abandoned, and is related U.S. application Ser. No. 448,672, filed on even date, now abandoned all of these disclosures being entirely incorporated by reference herein.

BACKGROUND OF THE INVENTION

The present invention is concerned with a combination of an aromatase-inhibitor and an antiandrogen for use in the prophylaxis and/or treatment by therapy of benign prostatic hyperplasia (BPH), and with pharmaceutical preparations and packs or kits suitable for such use.

Benign prostatic hyperplasia involves a benign enlargement of the prostate gland which starts in the so-called "inner" prostate gland. Discomfort can be attributed primarily to the obstructions of the urethra that occur. Voiding of the bladder is impeded and residual urine is retained. Without surgical treatment uremia may occur.

Up to now it has been almost impossible to treat this disorder, very frequent in older men, using medicaments. The phyto-preparations used for this purpose, such as, for example, $\beta$-sitosterin, mixtures of various plant extracts and combinations of plant extracts with the neurotropic spasmolysant azoniaspirochloride have proved ineffective in a one year study. Although the patients under therapy experienced an improvement in the micturition symptom, a regression of the hyperplastic prostate gland was not achieved.

Hormones, too, find application in the treatment of prostatic hyperplasia. Of these substances the depot gestagen gestonorone caproate is worthy of special mention. Compared with the phyto-preparations, an improved action is obtained with gestonorone caproate. The prolonged duration of micturition before the treatment is distinctly shortened and the maximum flow value (flow of urine per unit of time) is improved. A distinct reduction in the size of the adenoma cannot, however, be detected in this case either.

Prostatic hyperplasia involves a benign enlargement of the prostate gland, in which both the interstice (stroma) and the epithelium participate to a varying degree. Hormonal effects have been strongly implicated in the etiology. Heretofore, it has been presumed that abnormal levels of androgens contribute to the enlargement. As a result, antiandrogenic therapy has been suggested by many. See, e.g., U.S. Pat. No. 3,423,507 (e.g., administration of the antiandrogen, cyproterone acetate, i.e., $1\alpha$, $2\alpha$-methylene-6-chloro-$17\alpha$-acetoxy-6-dehydroprogesterone), U.S. Pat. No. 4,055,641, etc. More recently, evidence has been gathered which suggests that, inter alia, a shifting of the estrogen/androgen ratio in favor of estrogen may be regarded as a cause of BPH. That is, suggestions have been made that an increase in the estrogen level can contribute to the enlargement of the prostate. Thus, the state of the art establishes an expectation that an increase in the estrogen level and/or an increase in the androgen level will contribute toward BPH, while a shifting of the estrogen/androgen ratio in favor of the amount of estrogen, inter alia, may also be regarded as a cause of BPH. Moreover, various investigations have shown that in older men the concentrations of serum testosterone fall off; at the same time the proportion of SHBG (sex hormone binding globulin, specific transport protein for steroids) increases, so that the biological availability of androgens decreases still further.

Thus, the literature establishes an expectation of a benign enlargement of the prostate due to an increase in the estrogen level alone, an increase in the androgen level alone, or an increase in the estrogen/androgen ratio.

For example, in U.S. Pat. No. 4,310,523 it is proposed that a combination of an antiestrogen and an antiandrogen is effective for the prophylaxis and/or therapy of benign prostatic hyperplasia. This reference attests to the fact that both the effects of estrogen and the effects of androgen are important since medicaments directed against each are necessary. The method of this patent is disadvantageous since the physiological effect of the antiestrogens is highly dosage specific; for example, at relatively high doses, antiestrogens will act agonistically, i.e., as estrogens. Similarly, the mentioned treatment of U.S. Pat. No. 3,423,507 using gestagenically and antiandrogenically active esters such as cryproterone esters, is disadvantageous since only a partial regression of the hyperplasia is effected, no doubt due to the failure to treat the estrogenic factors. All of the evidence shows that both factors must be treated.

A further suggestion of the role of increased estrogen levels in the development of BPH is contained in the disclosures of H. U. Schweikert (1979): "Conversion of androstenedione to estrone in human fibroblasts cultured from prostate, genital and nongenital skin." Horm. Metab. Res. 11, 635–640; Schweikert, H. U., Hein, H. J. and F. H. Schroeder: "Androgen metabolism in fibroblasts from human benign prostatic hyperplasia, prostatic carcinoma and nongenital skin" in 'Steroid receptors, metabolism and prostatic cancer.' Editors: F. H. Schroeder and H. J. de Voogt, pages 126–133, Excerpta Medica (1980), International Congress Series No. 494, Amsterdam, Oxford, Princeton. These references report the results of studies showing that fibroblast cultures from human prostatic hyperplasia tissue are able to aromatize testosterone to form the corresponding estrogens more strongly than fibroblast cultures originating from healthy prostate tissue. The phenomenon of aromatization of androgens to form estrogens in the prostate gland is consistent with previous findings that estrogens present in men originate predominantly from peripheral aromatization of androgenic hormones and not from testicular biosynthesis, as contained in the disclosures of H. U. Schweikert: "Befunde zum Androgenmetabolismus" in 'Androgenisierungserscheinungen bei der Frau,' editors: J. Hammerstein, U. Lachnit-Fixson, F. Neumann and G. Plewig, pages 42–50, Excerpta Medica (1979), Amsterdam, Oxford, Princeton; MacDonald, P. C., Rombaut, R. P. and P. K. Siiteri (1967): "Plasma precursors of estrogen. I. Extent of conversion of plasma $\Delta^4$-androstenedione to estrone in normal males and nonpregnant normal, castrate and adrenalectomized females." J. Clin. Endocrinol. Metab. 27, 1103–1111; Weinstein, R.

L., Kelch, R. P., Jenner, M. R., Kaplan, S. L. and M. M. Grumbach (1974): "Secretion of unconjugated androgens and estrogens by the normal and abnormal testis before and after human chorionic gonadotropin." J. Clin. Invest. 53, 1-6.

It can thus be seen that BPH is a condition considered by the prior art to be caused both by increased estrogen levels and increased androgen levels or an increase in the estrogen/androgen ratio. The precise etiology has not yet been elucidated. Because of the existence of both estrogenic and androgenic factors, proposed hormonal treatments have been less than satisfactory and have not been predictable with any degree of reliability. For example, if one were to consider the possibility of inhibiting the aromitization of androgens into estrogens using any of the known aromatase-inhibitors, it could not be expected that such treatment would be successful. As indicated, an increase in the amount of androgens has been established as one cause of BPH. Since an aromatase-inhibitor would decrease the amount of estrogen, but at the same time would increase the relative amount of androgen, offsetting effects must be expected. In fact, studies involving a known aromatase-inhibitor confirm such offsetting effects. In these studies, it has been shown that the known aromatase-inhibitor, $\Delta^1$-testolactone(Teslac ®), does inhibit the conversion of androgens to estrogens, thereby causing a fall in the serum estrogen level; however, at the same time, it causes a rise in the serum androgen level. (See, e.g., R. A. Vigersky and A. R. Glass, "Effects of $\Delta^1$-Testolactone on the Pituitary-Testicular Axis In Oligospermic Men," J. Clin. Endocrin. and Metab., 52, 897–902 (1981); R. M. Barone, I. M. Shamonki, P. K. Siiteri, and H. L. Judd, "Inhibition of Peripheral Aromatization of Androstenedione to Estrone in Postmenopausal Women with Breast Cancer Using $\Delta^1$-Testolactone," J. Clin. Endocrin. and Metab., 49, 672–676 (1979); S. P. Marynick, D. L. Loriaux, R. J. Sherins, J. C. Pita, Jr., and M. B. Lipsett, "Evidence That Testosterone Can Suppress Pituitary Gonadotropin Secretion Independently of Peripheral Aromatization," J. Clin. Endocrin. and Metab., 49, 396–398 (1979); and P. K. Siiteri and E. Aubrey Thompson, "Studies of Human Placental Aromatase," J. Ster. Biochem., 6, 317–332 [1975].) Thus, administration of an aromatase-inhibitor (e.g., also including the aromatase-inhibitors disclosed in U.S. Pat. No. 4,235,893), would be expected to have a beneficial effect on BPH in view of the fact that it would lower estrogen levels; however, in view of the fact that its administration would be expected to increase androgen levels, it would be expected to have a negative influence on BPH. Accordingly, the prior art contains no suggestion that administration of an aromatase-inhibitor could be effective in treating BPH. Their use in the prior art has been restricted to indications involving increased estrogen levels only, and not increased androgen levels. (U.S. Pat. No. 4,235,893.)

Moreover, because administration of aromatase-inhibitors leads to an increase in androgen levels, it also would not be expected that co-administration of an aromatase-inhibitor and an antiandrogen would produce effective prophylaxis and/or treatment of BPH. It would be a priori counterproductive to administer an agent which increases the level of antagonistic androgen and then co-administer an antiandrogen to alleviate that negative effect. There is no basis for predicting that such treatment, in fact, would not cause a worsening of the condition. It would, moreover, be expected that the amount of antiandrogen to be co-administered in this unfavorable method would be greatly increased in comparison to the amount necessary in its coadministration with an antiestrogen in accordance with the prior art.

Since the prostate gland of men possesses estrogen receptors and the interstice (stroma) is a target organ for estrogens in BPH, the estrogens bring about the stimulation of the fibromuscular tissue. From this it follows that, in humans, prostatic hyperplasia stimulated by estrogens is predominantly a disorder of the fibromuscular interstice (stroma).

These findings are also supported by investigations carried out on dogs. It has been possible to show that estrogen treatment leads to a stimulation of the glandular epithelium (parenchyma) (Tunn, U. W., Schuering, B., Senge, Th., Neumann, F., Schweikert, H. U. and H. P. Rohr (1981): "Morphometric analysis of prostates in castrated dogs after treatment with androstanediol, estradiol and cyproterone acetate," Invest. Urol. 18: 289–292.) These studies also clearly show that both estrogenic effects and androgenic effects are important in BPH. Also, in autoradiographic studies on human prostatic hyperplasia tissue, it has been possible to show that it is only the glandular epithelium (parenchyma) that is a target organ for androgens, and not the interstice.

SUMMARY OF THE INVENTION

Accordingly, it is an object of this invention to provide an agent and method for treatment or prophylaxis of BPH in men.

Upon further study of the specification and appended claims, further objects and advantages of this invention will become apparent to those skilled in the art.

These objects have been achieved according to the present invention by using a combination of an aromatase-inhibitor with an antiandrogen which effects a regression both of the epithelial and of the fibromuscular parts of the prostate gland.

The present invention accordingly relates to the combination of an aromatase-inhibitor and an antiandrogen in a weight ratio of the aromatase-inhibitor to the antiandrogen of from about 20:1 to 1:1, preferably from 10:1 to 4:1, for use in a method of prophylaxis of prostatic hyperplasia and/or of treatment by therapy of prostatic hyperplasia and particularly to a method for the treatment of benign prostatic hyperplasia in a male human patient suffering therefrom, comprising administering to the patient an effective amount of a combination of an aromatase-inhibitor and an antiandrogen, or, to a method for the prophylaxis of benign prostatic hyperplasia in a male human patient not suffering from benign prostatic hyperplasia but in whom prophylactic treatment against benign prostatic hyperplasia is desired, comprising, administering to the patient an effective amount of a combination of an aromatase-inhibitor and an antiandrogen.

The aromatase-inhibitor and antiandrogen can be used either combined in a single form of administration or separately in two different forms of administration. They are preferably administered orally but may also be administered parenterally, especially intramuscularly.

The present invention accordingly also provides a pharmaceutical preparation suitable for use according to the present invention, which comprises an aromatase-inhibitor in admixture or conjunction with an antiandrogen, the ratio by weight of the aromatase-inhibitor to the antiandrogen being within the range of from about 20:1 to 1:1, preferably from 10:1 to 4:1.

The present invention further provides a pharmaceutical kit or pack suitable for use according to the present invention, which comprises discrete first and second parts, the first part comprising an aromatase-inhibitor in admixture or conjunction with a pharmaceutically suitable carrier and the second part comprising an antiandrogen in admixture or conjunction with a pharmaceutically suitable carrier, the ratio by weight of the aromatase-inhibitor to the antiandrogen in the pack being within the range of from about 20:1 to 1:1, preferably from 10:1 to 4:1.

DETAILED DISCUSSION

By using an aromatase-inhibitor, it is believed that the formation of biologically active estrogens is prevented. As a result, the stimulation of the fibromuscular tissue is forestalled, and a regression with a decrease in size and, consequently, the desired improvement in the clinical symptoms (e.g., micturition discomfort) occurs. In addition, it is believed that the antiandrogen leads to a regression of the epithelial part of the prostate gland. By treatment with a combination of an aromatase-inhibitor and an antiandrogen, therefore, the growth of both types of prostate tissue responsible for the development of the syndrome is inhibited.

Suitable for use according to the present invention are all substances that act as aromatase-inhibitors, i.e., those which act as a substrate for an aromatase. They themselves must not possess estrogenic or other hormonal actions in addition to their action on the aromatization. Also, the products of the aromatization produced from them must also possess essentially no estrogenic or other hormonal actions.

Suitable such aromatase-inhibitors include testolactone (17a-oxa-D-homo-androsta-1,4-diene-3,17-dione);

There may also be mentioned as the aromatase-inhibitor, for example, the following known compounds:
androsta-4,6-diene-3,17-dione,
androsta-4,6-dien-17β-ol-3-one acetate,
androsta-1,4,6-triene-3,17-dione,
androst-4-ene-19-chloro-3,17-dione,
androst-4-en-17β-ol-3-one acetate,
androst-4-en-17β-ol-3-one formate,
androst-4-en-17β-ol-3-one propionate and
androst-4-ene-3,6,17-trione, and also
androst-4-en-4-ol-3,17-dione and esters thereof,
for example the actetate, heptanoate, dodecanoate, hemisuccinate and benzoate and others disclosed in Endo. 92 (1973) 866–880 and U.S. Pat. No. 4,235,893, e.g., generally, the $C_{2-12}$-alkanoates, whose disclosure is incorporated by reference herein.

Of course, the aromatase itself of which the compound to be administered by this invention must be an inhibitor, is any aromatase found in the human male which effects aromatization of a compound to form an estrogenic substance.

The daily dose for male human beings of the aromatase-inhibitor is 10 mg to 400 mg, preferably 50 mg to 250 mg, of testolactone (17a-oxa-D-homo-androsta-1,4-diene-3,17-dione), or an amount of another aromatase-inhibitor that is biologically equivalent to these amounts of testalactone.

Biologically equivalent amounts of aromatase inhibitors can be determined using any conventional protocol or procedure permitting a determination of the aromatization inhibition achieved by a compound such as those procedures described in the foregoing references relating to aromatase-inhibitors and their effects. A particularly preferred such protocol is disclosed in Brueggemeier et al, J. of Med. Chem., 1978, Vol 21, No. 10, p. 1007, whose disclosure is incorporated by reference herein. That is, equivalent amounts can be determined using fully conventional procedures employed in differential potency determinations.

Suitable for use according to the present invention as antiandrogens are both steroidal compounds and also non-steroidal compounds having antiandrogenic activity. Such activity can be determined by any conventional protocol such as that disclosed by Hershberger et al, Proc. Soc. Exp. Biol. (N.Y.), 83, (1952), p. 175, whose disclosure is incorporated by reference herein.

Suitable steriodal antiandrogens include compounds of formula (I)

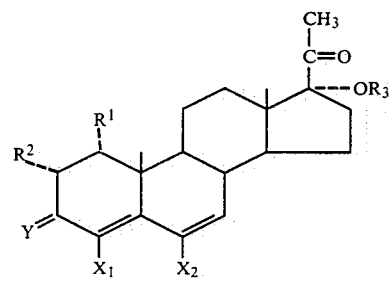

in which
$R^1$ and $R^2$ each is hydrogen or together represent a carbon-to-carbon bond or methylene
$R^3$ is an acyl group derived from an acid customarily used in steroid chemistry in esterifying OH,
Y is oxygen or

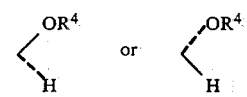

wherein
$R^4$ is hydrogen, acyl as defined for $R^3$, or alkyl,
$X_1$ is hydrogen or chlorine and
$X_2$ is hydrogen, fluorine or chlorine;
and compounds of formula (II)

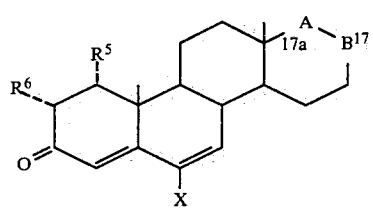

wherein
$R^5$ and $R^6$ each is hydrogen or together represent methylene,
X is hydrogen, fluorine or chlorine and
A-B is

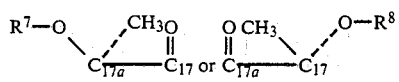

in which $R^7$ and $R^8$ each is acyl as defined above.

Suitable acyl groups in the above, e.g., for $R^3$, $R^4$, $R^7$ and $R^8$, include acyl groups of acids commonly used in steroid chemistry for the esterification of secondary and tertiary hydroxyl groups. Preferred are acyl groups of aliphatic carboxylic acids containing 1 to 8 carbon atoms, for example acetic acid, propionic acid, butyric acid, valeric acid, isovaleric acid, caproic acid and enanthic acid. The esters of acetic acid are especially preferred.

Suitable alkyl groups $R^4$ include lower alkyl groups containing 1 to 5 carbon atoms, the methyl group being preferred.

Such compounds are fully conventional and are described, for example, in the following references: compounds of formula (I), for example, in U.S. Pat. Nos. 3,234,093; 3,076,823; 3,549,671; 3,789,087 and in British Pat. Nos. 890,315; 1,005,495; 1,049,026 and 1,172,086; and compounds of formula (II), for example, in U.S. Pat. No. 3,492,338, the disclosures of all of which are incorporated by reference herein.

Typical compounds of formula (I) are the 17-esters of, for example, the compounds listed in the following Table:

Table I 6-chloro-17-hydroxy-1α,2α-methylene-pregna-4,6-diene-3,20-dione, 6-chloro-17-hydroxy-pregna-4,6-diene-3,20-dione, 6-chloro-17-hydroxy-pregna-1,4,6-triene-3,20-dione, 6-chloro-3ξ,17-dihydroxy-1α,2α-methylene-pregna-4,6-dien-20-one, 6-chloro-3ξ-methoxy-17-hydroxy-1α,2α-methylene-pregna-4,6-dien-20-one, 6-fluoro-17-hydroxy-1α,2α-methylene-pregna-4,6-diene-3,20-dione, 17-hydroxy-1α,2α-methylene-pregna-4,6-diene-3,20-dione or 4,6-dichloro-17-hydroxy-1α,2α-methylene-pregna-4,6-diene-3,20-dione.

Preferred compounds of formula (I) are 6-chloro-17-hydroxy-1α,2α-methylene-pregna-4,6-diene-3,20-dione acetate (cyproterone acetate) and 6-chloro-17-hydroxy-pregna-4,6-diene-3,20-dione acetate (chlormadinone acetate).

Typical compounds of formula (II) are, for example, 6-chloro-17aβ-acetoxy-17aα-methyl-1α,2α-methylene-D-homo-Δ$^{4,6}$-androstadiene-3,17-dione and 6-chloro-17α-acetoxy-17β-methyl-1α,2α-methylene-D-homo-Δ$^{4,6}$-androstadiene-3,17a-dione.

Suitable non-steroidal antiandrogens include the compounds
2-methyl-N-[4-nitro-3-(trifluoromethyl)-phenyl]-propionamide (flutamide)

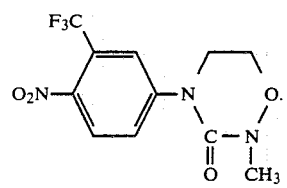
(III)

2-hydroxy-2-methyl-N-[4-nitro-3-(trifluoromethyl)-phenyl]-propioamide

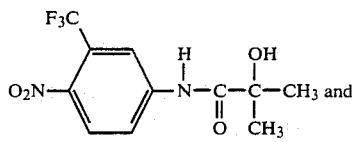
(IV)

2-methyl-4-[4-nitro-3-(trifluoromethyl)-phenyl]-5,6-dihydro-2H-1,2,4-oxadiazine-3-one

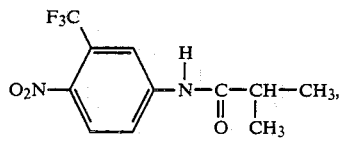
(V)

The daily dose for male human beings of the antiandrogen is approximately 1 to 100 mg, preferably 5 to 40 mg, of cyproterone acetate or an amount of another antiandrogen that is biologically equivalent thereto. Biological equivalence here can be determined by any conventional pharmocological protocol for antiandrogenic activity, e.g., as discussed in the Hershberger reference above. Usually the amount will fall within the same weight range.

The pharmaceutical preparations of the present invention and each of the first and second parts of the pharmaceutical kits of the present invention may be in a form suitable for oral or parenteral administration. The active substances may be processed by methods known per se into the customary forms of administration with, for example, the additives, carrier substances and/or taste correctives customarily used in galenical pharmacy.

For the preferred oral administration there are suitable, more especially, tablets, dragees, capsules, pills, suspensions or solutions. If desired, the pharmaceutical preparations of the present invention may be in the form of two-layer tablets, one layer of each tablet comprising the aromatase-inhibitor and the other layer comprising the antiandrogen.

For parenteral, especially intramuscular, administration, oily solutions are suitable, for example sesame oil or castor oil solutions. Solubilizers, for example benzyl benzoate or benzyl alcohol, may be added to increase solubility. The oily solutions may, if desired, be stored in ampules.

The pharmacologically active compounds of this invention can be processed in accordance with conventional methods of galenic pharmacy to produce medicinal agents for administration to humans. Conventional excipients are pharmaceutically acceptable organic or inorganic carrier substances suitable for parenteral or enteral application which do not deleteriously react with the active compounds. Suitable pharmaceutically acceptable carriers include but are not limited to water, salt solutions, alcohols, gum arabic, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxymethylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, ampules are convenient unit dosages.

For enteral application, particularly suitable are tablets, dragees, suppositories, or capsules having talc and/or a carbohydrate carrier or binder or the like, the carrier preferably being lactose and/or corn starch and/or potato starch. A syrup, elixir or the like can be used wherein a sweetened vehicle is employed. Dosages for a given host can be determined using conventional considerations, e.g., by customary comparison of the differential activities of the subject compound and of another agent, e.g., testolactone or cyproterone acetate by means of an appropriate, conventional pharmacological protocol. Administration in accordance with this invention is conventional except where indicated otherwise herein.

The pharmaceutical preparations of the present invention may be in unit dosage form, each dosage unit advantageously containing (i) an amount of the aromatase-inhibitor that is biologically equivalent to 10 to 400 mg, preferably 50 to 250 mg, of testolactone and (ii) an amount of the antiandrogen that is biologically equivalent to 1 to 100 mg, preferably 5 to 40 mg, of cyproterone acetate. Similarly, each of the first and second parts of the pharmaceutical packs or kits of the present invention may be in unit dosage form, each dosage unit in the first and second parts containing a corresponding amount of the aromatase-inhibitor or antiandrogen, respectively.

The unit dosage pharmaceutical preparations and packs formulated as stated above contain per unit dosage unit, when in a form suitable for oral administration, preferably from 10 mg to 250 mg of testolactone and from 1 mg to 50 mg of cyproterone acetate and, when in a form suitable for parenteral administration, preferably from 20 mg to 200 mg of testolactone and from 5 mg to 100 mg of cyproterone acetate, or the biologically equivalent doses in each case of another aromatase-inhibitor and another antiandrogen.

The present invention further provides a pharmaceutical pack which comprises an aromatase-inhibitor and an antiandrogen, the ratio by weight of the aromatase-inhibitor to the antiandrogen being within the range of from substantially 20:1 to 1:1, preferably from 10:1 to 4:1, together with instructions for their use in the prophylaxis and/or therapy of prostatic hyperplasia.

The same administration characteristics also apply to the use of the pharmaceutical preparation of this invention in the prophylaxis of BPH. Such administration will be dictated for a given patient as usual where a doctor has conventionally determined that the patient has an abnormally high risk of developing BPH, e.g., where the patient has a family history of BPH or where the patient has reached an advanced age. The onset of prophylactic administration in the adult human male will usually be in the range of 50–65 years.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

| Composition of a tablet | |
|---|---|
| 5.0 mg | of 17a-oxa-D-homo-androsta-1,4-diene-3,17-dione (testolactone) |
| 5.0 mg | of 6-chloro-17-hydroxy-1α,2α-methylene-pregna-4,6-diene-3,20-dione acetate (cyproterone acetate) |
| 115.0 mg | of lactose |
| 50.0 mg | of maize starch |
| 2.5 mg | of poly-N-vinylpyrrolidone 25 |
| 2.0 mg | of Aerosil |
| 0.5 mg | of magnesium stearate |
| 225.0 mg | total weight of the tablet, which was manufactured in the customary manner on a tablet press. If desired, the testolactone and cyproterone acetate may also be compressed separately with in each case half of the above-specified additives to form a two-layer tablet. |

EXAMPLE 2

| Composition of a tablet | |
|---|---|
| 20.0 mg | of 17a-oxa-D-homo-androsta-1,4-diene-3,17-dione (testolactone) |
| 5.0 mg | of 6-chloro-17-hydroxy-1α,2α-methylene-pregna-4,6-diene-3,20-dione acetate (cyproterone acetate) |
| 135.0 mg | of lactose |
| 60.0 mg | of maize starch |
| 2.5 mg | of poly-N-vinylpyrrolidone 25 |
| 2.0 mg | of Aerosil |
| 0.5 mg | of magnesium stearate |
| 225.0 mg | total weight of the tablet, which was manufactured in the customary manner on a tablet press. If desired, the testolactone and cyproterone acetate may also be compressed separately with in each case half of the above-specified additives to form a two-layer tablet. |

EXAMPLE 3

| Composition of an oily solution: |
|---|
| 100.0 mg of testolactone |
| 20.0 mg of cyproterone acetate |
| 343.4 mg of castor oil |
| 608.6 mg of benzyl benzoate |
| 1072.0 mg = 1 ml |

An ampule was filled with the solution. If desired, the testolactone and cyproterone acetate may also be introduced separately into two compartments with in each case half of the above-specified additives, so that one of the compartments contains the testolactone and the other contains the cyproterone acetate.

EXAMPLE 4

Examples 2 and 3 are repeated except that, in each case, testolactone is replaced by one of the aromatase-inhibitors mentioned above and cyproterone acetate is replaced by one of the antiandrogens mentioned above.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A pharmaceutical composition comprising an aromatase-inhibitor and an antiandrogen in a weight ratio of the aromatase-inhibitor to the antiandrogen of from about 20:1 to about 1:1, wherein the total amount of active ingredients is effective for the prophylaxis or treatment of benign prostatic hyperplasia, and wherein the aromatase inhibitor possesses essentially no hormonal effects and products of the aromatization therewith in the patient possess essentially no hormonal effects.

2. A composition of claim 1 further comprising a pharmaceutically acceptable carrier.

3. A composition of claim 1, wherein the weight ratio of the aromatase-inhibitor to the antiandrogen is 10:1 to 4:1.

4. A composition of claim 2 wherein the amount of the aromatase-inhibitor is biologically equivalent to 10 to 400 mg of testolactone and the amount of the antiandrogen is biologically equivalent to 1 to 100 mg of cyproterone acetate.

5. A composition of claim 4 wherein the amount of the aromatase-inhibitor is biologically equivalent to 50 to 250 mg of testolactone and the amount of the antiandrogen is biologically equivalent to 5 to 40 mg of cyproterone acetate.

6. A composition of claim 2 wherein the aromatase-inhibitor is testolactone.

7. A composition of claim 2 wherein the aromatase-inhibitor is androsta-4,6-diene-3,17-dione, androsta-4,6-dien-17β-ol-3-one acetate, androsta-1,4,6-triene-3,17-dione, androst-4-ene-19-chloro-3,17-dione, or androst-4-ene-3,6,17-trione.

8. A composition of claim 2 wherein the aromatase-inhibitor is androst-4-en-4-ol-3,17-dione or a 4- ester thereof.

9. A composition of claim 8 wherein the aromatase-inhibitor is androst-4-en-4-ol-3,17-dione.

10. A composition of claim 8 wherein the aromatase-inhibitor is a $C_{2-12}$- alkanoate, hemisuccinate or benzoate ester.

11. A composition of claim 10 wherein the ester is the acetate, heptanoate, dodecanoate, hemisuccinate or benzoate.

12. A compositon of claim 2, 6, or 8 wherein the antiandrogen is a compound of the formula

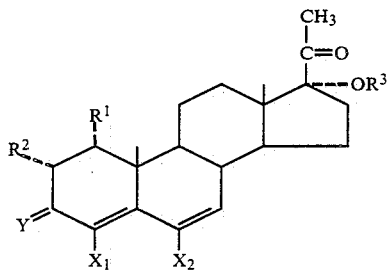

wherein $R^1$ and $R^2$ each is hydrogen or together represent a carbon-to-carbon bond or methylene $R^3$ is $C_{1-8}$-alkanoyl, Y is oxygen or

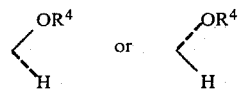

wherein $R^4$ is hydrogen, $C_{1-8}$-alkanoyl or $C_{1-5}$- alkyl, $X_1$ is hydrogen or chlorine and $X_2$ is hydrogen, fluorine or chlorine.

13. A composition of claim 12 wherein each alkanoyl group is acetyl and each alkyl group is methyl.

14. A composition of claim 12 wherein the antiandrogen is a 17-ester of 6-chloro-17-hydroxy-1α,2α-methylene-pregna-4,6-diene-3,20-dione, 6-chloro-17-hydroxy-pregna-4,6-diene-3,20-dione, 6-chloro-17-hydroxy-pregna-1,4,6-triene-3,20-dione, 6-chloro-3ξ,17-dihydroxy-1α,2α-methylene-pregna-4,6-dien-20-one, 6-chloro-3 -methoxy-17-hydroxy-1α,2α-methylene-pregna-4,6-dien-20-one, 6-fluoro-17-hydroxy-1α,2α-methylene-pregna-4,6-diene-3,20-dione, 17-hydroxy-1α,2α-methylene-pregna-4,6-diene-3,20-dione or 4,6-dichloro-17-hydroxy-1α,2α-methylene-pregna-4,6-diene-3,20-dione.

15. A composition of claim 12 wherein the antiandrogen is cyproterone acetate.

16. A composition of claim 12 wherein the antiandrogen is chlormadinone acetate.

17. A composition of claim 6 wherein the antiandrogen is cyproterone acetate in an amount of 5–100 mg and the amount of testolactone is 20–200 mg.

18. A composition of claim 2, 6, or 8 wherein the antiandrogen is a compound of the formula

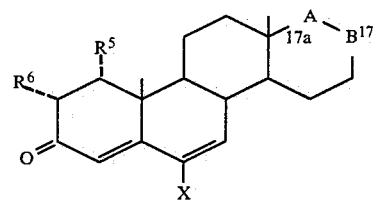

wherein $R^5$ and $R^6$ each is hydrogen or together represent methylene,

X is hydrogen, fluorine or chlorine and

A-B is

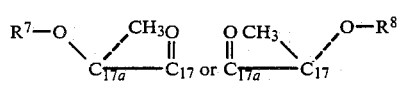

wherein $R^7$ and $R^8$ each is $C_{1-8}$ alkanoyl.

19. A composition of claim 18 wherein $R^7$ and $R^8$ each is acetyl.

20. A composition of claim 18 wherein the antiandrogen is 6-chloro-17aβ-acetoxy-17aα-methyl-1α,2α-methylene-D-homo-Δ$^{4,6}$-androstadiene-3,17-dione.

21. A composition of claim 18 wherein the antiandrogen is 6-chloro-17α-acetoxy-17β-methyl-1α,2α-methylene-D-homo-Δ$^{4,6}$-androstadiene-3,17a-dione.

22. A composition of claim 1 wherein the antiandrogen is 2-methyl-N-[4-nitro-3-(trifluoromethyl)-phenyl]-propionamide.

23. A composition of claim 1 wherein the antiandrogen is 2-hydroxy-2-methyl-N-[4-nitro-3-(trifluoromethyl)-phenyl]-propionamide.

24. A composition of claim 1 wherein the antiandrogen is 2-methyl-4-[4-nitro-3-(trifluoromethyl)-phenyl]-5,6-dihydro-2H-1,2,4-oxadiazine-3-one.

25. A composition of claim 2 in a form suitable for oral administration.

26. A composition of claim 2 in the form of a two-layer tablet, one layer comprising the aromatase-inhibitor and the other layer comprising the antiandrogen.

27. A pharmaceutical composition of claim 2 in the form of a kit comprising discrete first and second parts, the first part comprising an aromatase-inhibitor in admixture or conjunction with a pharmaceutically suitable carrier and the second part comprising an antiandrogen in admixture or conjunction with a pharmaceutically suitable carrier, the ratio by weight of the aromatase-inhibitor to the antiandrogen in the pack being within the range of about 20:1 to about 1:1.

28. A method for the treatment of benign prostatic hyperplasia in a male human patient suffering therefrom comprising, administering to the patient an amount of a composition of claim 1, 2, 6, 8, 12, 15, 16, 17, or 18 effective to treat benign prostatic hyperplasia.

29. A method for the prophylaxis of benign prostatic hyperplasia in a male human patient not suffering from benign prostatic hyperplasia but in whom prophylactic treatment against benign prostatic hyperplasia is desired, comprising, administering to the patient an amount of a composition of claim 1, 2, 6, 8, 12, 15, 16, 17, or 18 effective to prevent benign prostatic hyperplasia.

30. A composition of claim 1, wherein the aromatase inhibitor is not androst-4-ene-19-(al or ol)-3,17-dione.

31. A method of claim 28/1, wherein the aromatase inhibitor is not androst-4-ene-19-(al or ol)-3,17-dione.

32. A composition of claim 1, wherein the compound administered as said aromatase inhibitor was not per se previously administered for the treatment of benign prostatic hyperplasia.

33. A method of claim 28/1, wherein the compound administered as said aromatase inhibitor was not per se previously administered for the treatment of benign prostatic hyperplasia.

34. A composition of claim 1, wherein the compound administered as said aromatase inhibitor was evaluated to determine its aromatase inhibition efficacy and on the basis of the resultant determined efficacy was selected as said aromatase inhibitor to be used in said method.

35. A method of claim 28/1, wherein the compound administered as said aromatase inhibitor was evaluated to determine its aromatase inhibition efficacy and on the basis of the resultant determined efficacy was selected as said aromatase inhibitor to be used in said method.

36. A composition of claim 1, wherein the compound administered as said aromatase inhibitor was previously known to treat benign prostatic hypertrophy but not as an aromatase inhibitor, and the compound was tested to determine its aromatase inhibition efficacy prior to administration in said method.

37. A method of claim 28/1, wherein the compound administered as said aromatase inhibitor was previously known for the treatment of benign prostatic hypertrophy but not as an aromatase inhibitor, and the compound was tested to determine its aromatase inhibition efficacy prior to administration in said method.

38. A method of claim 28/1, further comprising, prior to said administering, evaluating the aromatase inhibitor compound to determine its aromatase inhibition efficacy and on the basis of the resultant determined efficacy, selecting said compound as the aromatase inhibitor in said method.

39. A method of claim 28/1, wherein the compound administered as said aromatase inhibitor was previously known for the treatment of benign prostatic hypertrophy but not as an aromatase inhibitor,
and further comprising, prior to said administering, testing the compound to determine its aromatase inhibition efficacy.

40. A pharmaceutical composition comprising an aromatase-inhibitor and an antiandrogen in a weight ratio of the aromatase-inhibitor to the antiandrogen of from about 20:1 to about 1:1, wherein the total amount of active ingredients is effective for the prophylaxis or treatment of benign prostatic hyperplasia; and wherein the aromatase inhibtiro possesses essentially no estrogenic effects and products of the aromatization therewith in the patient possess essentially no estrogenic effects.

41. A method for the treatment of benign prostatic hyperplasia in a male human patient suffering therefrom, comprising, administering to the patient an amount of a composition of claim 40 effective to treat benign prostatic hyperplasia.

42. A composition of claim 40 wherein the aromatase inhibitor also has essentially no androgenic effects and products of the aromatization therewith in the patient possess essentially no androgenic effects.

43. A method of claim 41 wherein the aromatase inhibitor also has essentially no androgenic effects and products of the aromatization therewith in the patient possess essentially no androgenic effects.

44. A pharmaceutical composition comprising an aromatase-inhibitor and an antiandrogen in a weight ratio of the aromatase-inhibitor to the antiandrogen of from about 20:1 to about 1:1, wherein the total amount of active ingredients is effective for the prophylaxis or treatment of benign prostatic hyperplasia; and wherein the aromatase inhibitor possesses an estrogenic effect lower than that of natural estrogen in the patient and products of the aromatization therewith in the patient possess estrogenic effects lower than that of natural estrogen in the patient.

45. A method for the treatment of benign prostatic hyperplasia in a male human patient suffering therefrom, comprising, administering to the patient an amount of a composition of claim 44 effective to treat benign prostatic hyperplasia.

46. A composition of claim 44 wherein the aromatase inhibitor also has an androgenic effect lower that that of natural androgen in the patient and products of the aromatization therewith in the patient possess androgenic effects lower than that of natural androgen in the patient.

47. A method of claim 45 wherein the aromatase inhibitor also has an androgenic effect lower than that of natural androgen in the patient and products of the aromatization therewith in the patient possess androgenic effects lower than that of natural androgen in the patient.

* * * * *